United States Patent
Linker

(10) Patent No.: US 8,353,091 B2
(45) Date of Patent: Jan. 15, 2013

(54) STUN GUN DART ACTIVE RETRIEVAL SYSTEM

(75) Inventor: Carson L. Linker, Camas, WA (US)

(73) Assignee: Global Pathogen Solutions, Inc., Camas, WA (US)

( * ) Notice: Subject to any disclaimer, the term of this patent is extended or adjusted under 35 U.S.C. 154(b) by 1078 days.

(21) Appl. No.: 12/069,132

(22) Filed: Feb. 7, 2008

(65) Prior Publication Data

US 2008/0140027 A1   Jun. 12, 2008

Related U.S. Application Data

(63) Continuation-in-part of application No. 11/269,409, filed on Nov. 8, 2005, now Pat. No. 7,520,248, which is a continuation-in-part of application No. 10/909,704, filed on Aug. 2, 2004, now Pat. No. 7,090,196.

(51) Int. Cl.
| | |
|---|---|
| *B23C 1/00* | (2006.01) |
| *B23P 19/04* | (2006.01) |
| *B24C 11/00* | (2006.01) |
| *G01N 21/00* | (2006.01) |
| *B66F 3/00* | (2006.01) |
| *B66F 15/00* | (2006.01) |
| *G01L 5/14* | (2006.01) |

(52) U.S. Cl. .............. 29/255; 29/55; 29/240; 254/18; 254/19; 73/167

(58) Field of Classification Search .............. 29/255, 29/240, 401, 427, 55; 119/174; 73/167, 73/102, 501, 512, 513; 254/18, 19, 20, 25
See application file for complete search history.

(56) References Cited

U.S. PATENT DOCUMENTS

| | | | | |
|---|---|---|---|---|
| 2,460,290 | A * | 2/1949 | Holcomb | 73/167 |
| 3,750,257 | A * | 8/1973 | Berecz | 29/813 |
| 4,044,771 | A * | 8/1977 | Wannag | 606/210 |
| 4,459,728 | A * | 7/1984 | Gaquere | 29/240 |
| 5,068,954 | A * | 12/1991 | Houska | 29/240 |
| 5,336,229 | A * | 8/1994 | Noda | 606/144 |
| 5,368,600 | A * | 11/1994 | Failla et al. | 606/139 |
| 5,438,741 | A * | 8/1995 | Ni | 29/240 |
| 5,467,247 | A * | 11/1995 | de Anda et al. | 361/232 |
| 5,495,630 | A * | 3/1996 | Estein et al. | 7/138 |
| 5,582,617 | A * | 12/1996 | Klieman et al. | 606/170 |
| 5,797,927 | A * | 8/1998 | Yoon | 606/144 |
| 5,937,557 | A * | 8/1999 | Bowker et al. | 42/70.01 |
| 5,962,806 | A * | 10/1999 | Coakley et al. | 102/502 |
| 6,406,440 | B1 * | 6/2002 | Stefanchik | 600/562 |
| 6,443,952 | B1 * | 9/2002 | Mulier et al. | 606/49 |
| 6,663,641 | B1 * | 12/2003 | Kovac et al. | 606/144 |
| 6,964,662 | B2 * | 11/2005 | Kidooka | 606/52 |

(Continued)

*Primary Examiner* — Lee D Wilson
*Assistant Examiner* — Alvin Grant
(74) *Attorney, Agent, or Firm* — Timothy E Siegel Patent Law, PLLC; Timothy E Siegel

(57) ABSTRACT

A stun gun dart acquiring, removing and housing device and method of using this device to remove a dart. The device provides a container, such as a tube, and a slider supported at least partially inside the container and is adapted to grasp a stun gun dart. The user places the slider over the dart, thereby engaging the dart into the distal end of slider and then moves the device away from subject, removing the dart. Then, the user moves the slider rearward into the container to store the dart in a safe location. The dart once locked in place inside the container can now be handled and viewed without concern of inadvertent contamination.

17 Claims, 3 Drawing Sheets

U.S. PATENT DOCUMENTS

| | | | |
|---|---|---|---|
| 7,090,196 B1 * | 8/2006 | Linker | 254/1 |
| 7,152,990 B2 * | 12/2006 | Kukuk | 362/112 |
| 7,314,471 B2 * | 1/2008 | Holman | 606/167 |
| 7,434,517 B1 * | 10/2008 | Linker | 102/502 |
| 7,520,248 B1 * | 4/2009 | Linker | 119/174 |
| 7,524,076 B2 * | 4/2009 | Kukuk | 362/112 |
| 7,879,046 B2 * | 2/2011 | Weinert et al. | 606/139 |
| 7,879,048 B2 * | 2/2011 | Bain et al. | 606/144 |
| 7,922,739 B2 * | 4/2011 | Downey | 606/174 |
| 7,935,052 B2 * | 5/2011 | Dumbauld | 600/205 |
| 2002/0139182 A1 * | 10/2002 | Duke | 73/167 |

* cited by examiner

STUN GUN DART ACTIVE RETRIEVAL SYSTEM

RELATED APPLICATIONS

This application is a continuation-in-part of application Ser. No. 11/269,409, filed Nov. 8, 2005, now U.S. Pat. No. 7,520,248 which, in turn, is a continuation-in-part of application Ser. No. 10/909,704 filed Aug. 2, 2004, now U.S. Pat. No. 7,090,196.

BACKGROUND OF THE INVENTION

The proliferation of stun guns among law enforcement, security forces and facilities for holding humans and animals throughout the world, has caused an unanticipated problem. Stun guns, such as the Taser® gun, work by shooting barbed darts into the subject. These darts are connected to thin wires, through which a series electric pulses is passed to subdue the subject.

After the subject has been subdued, it is necessary for a trained professional to remove the dart(s) from the subject. This is typically done after the subject is restrained with a device. The darts are then removed by holding the subject still with one hand, while removing the dart with the other. Unfortunately, during this operation the subject may suddenly move due to the pain or in an effort to gain freedom. This, in turn, may throw the responding professional off balance to the point that he inadvertently jabs the barbed end of the newly removed and contaminated dart into the hand or other part of the body used to stabilize the subject's body.

Far from being a minor, temporary injury, this brief event may have a life-long and tragically life-shortening effect on the responding professional, who may contract hepatitis, HIV or any one out of a long list of blood born pathogens from blood on the dart. This very occurrence has become all too common, with thousands of people all infected with a deadly virus through this mechanism or a related cause, such as an intra venous needle stick. Moreover, to avoid exposure to a blood-borne pathogens, many jurisdictions have instituted a procedure in which the agency who deployed the stun gun darts will call the fire department, paramedics or other trained professionals to acquire and remove the stun gun darts. This procedure is extremely costly in man hours, fuel, etc. Some way must be found to make the removal of stun gun darts safer for the personnel who must acquire, remove and store them.

SUMMARY

The present invention is a stun gun dart removing device and a method of using this device to acquire, remove and house stun gun darts. The device provides a container, such as a tube, and a slider supported in the container and which is adapted to grasp a stun gun dart. The user places the slider over the dart, thereby locking the dart into the end of the slider. The tool is then pulled away from the subject, removing the dart. The slider is then moved to the rear of the container to secure the dart in the container. This isolates the dart from the public health officers, and permits the safe handling of the dart, within the container, by any of a potential chain of people processing the dart as evidence or for reporting purposes. In a preferred embodiment the container has transparent sides, so the dart may be viewed by those handling the container.

An exemplary device embodying the device that forms a part of the invention is shown in the drawings described below, and is described in the following detailed description.

BRIEF DESCRIPTION OF THE DRAWINGS

The following drawings show an exemplary version of the device, but many other embodiments are possible.

DETAILED DESCRIPTION OF THE PREFERRED EMBODIMENT

Figure 1:
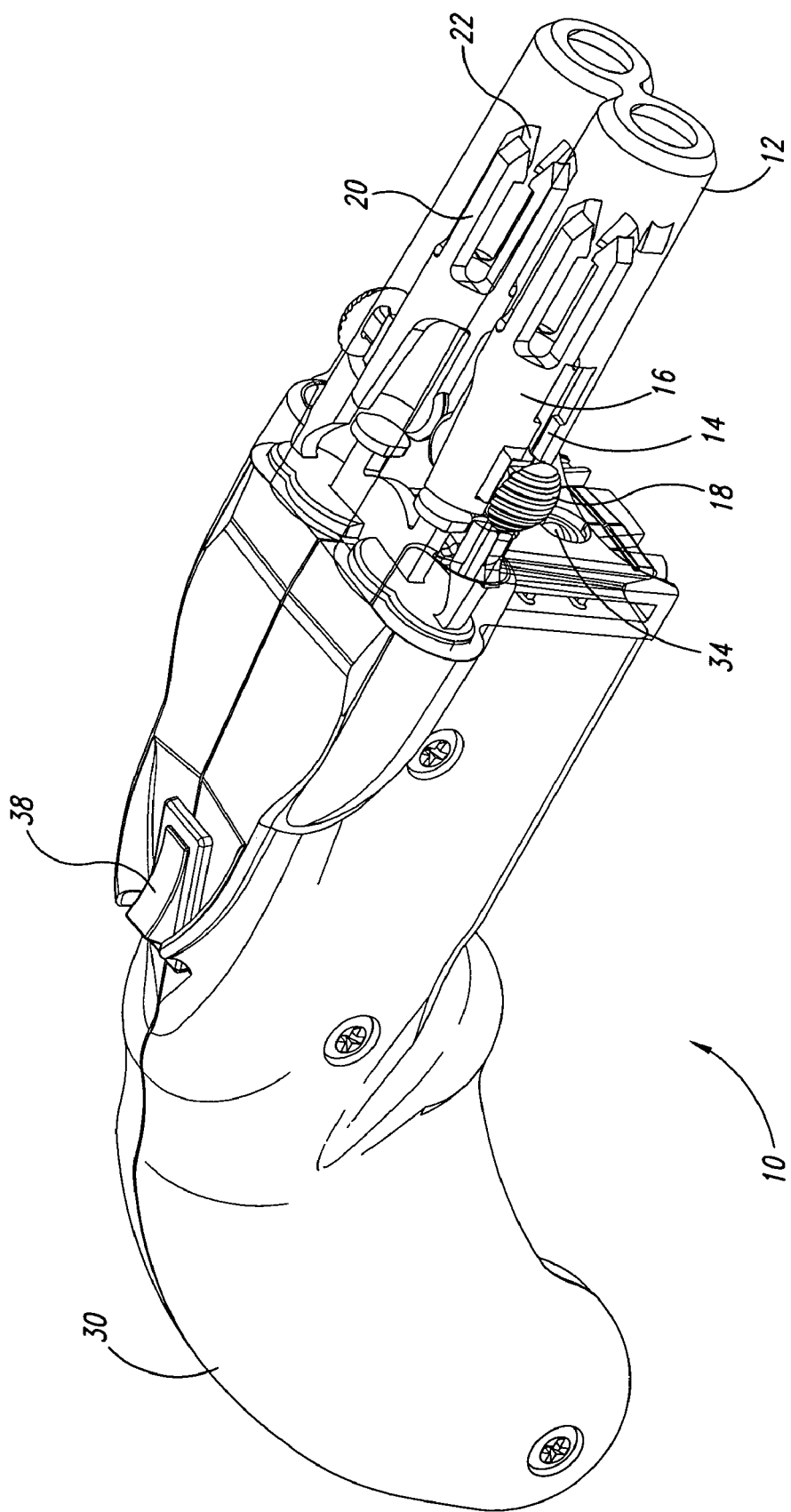
FIG. 1 is a perspective view of a stun gun dart removing device, according to the present invention.
Figure 2:
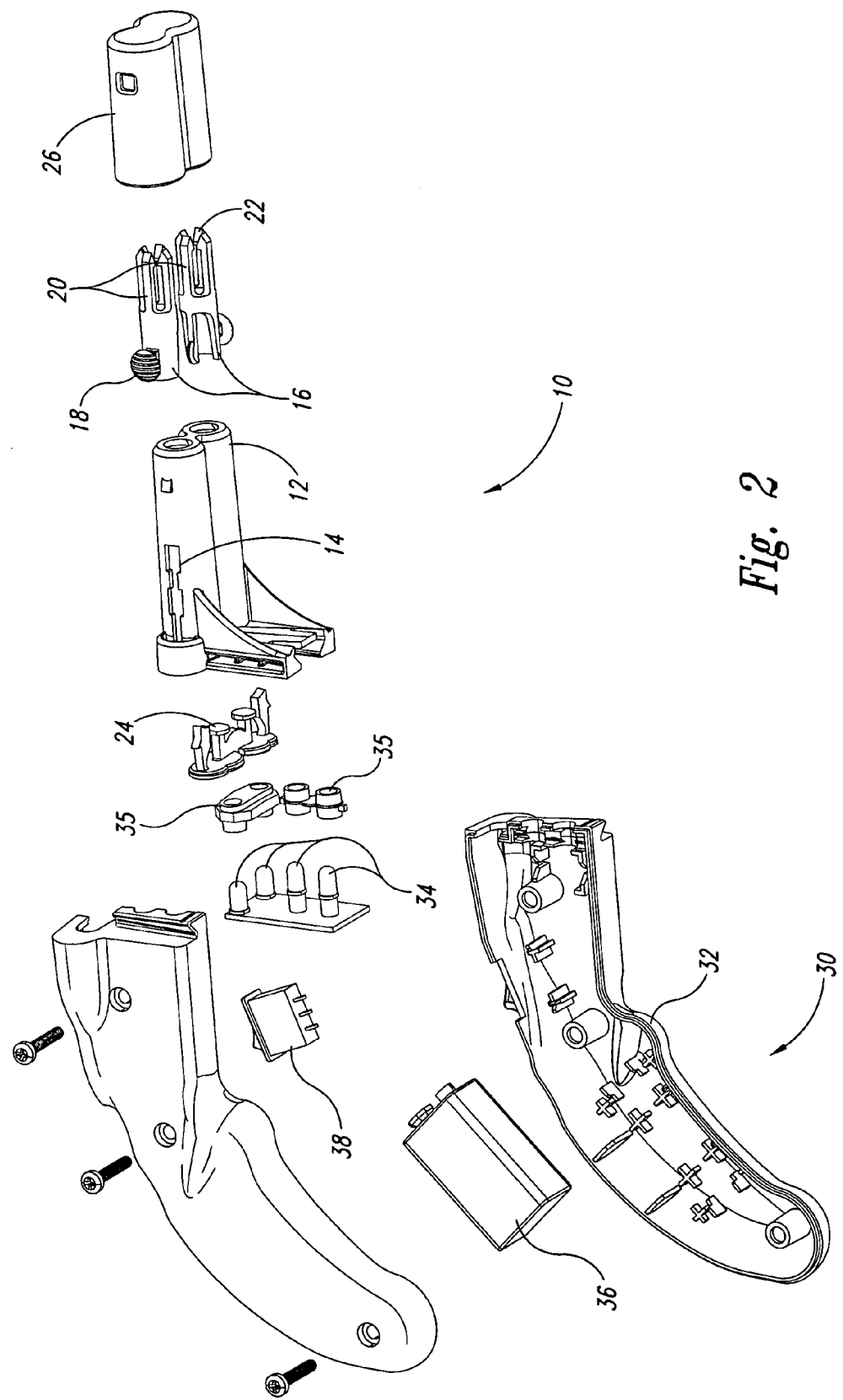
FIG. 2 is an exploded view, showing the parts of the device of FIG. 1.

Referring to FIGS. 1 and 2, a stun gun removal assembly 10 according to the present invention includes a pair of transparent containers, in the form of tubes 12, both having an interior diameter that tapers inwardly from back to front and defining a side slot 14. A slider 16 having a side tab 18 threaded through the side slot 14, is set into each tube 12. Forward facing arms 20 of sliders 16, have inwardly facing bumps 22 and are adapted to surround and grasp a dart. Each tube 12 has a removable rear closure 24 (FIG. 2), for accessing captured darts. A cap 26 (FIG. 2) for each tube 12, helps to secure a captured dart.

A handle 30 supports tubes 12 and doubles as a source of illumination. Handle 30 is made of two polymer molded halves 32 (FIG. 2), fastened together with screws. A set of light emitting diodes (LEDs) 34 are held in place by grommets 35 (FIG. 2), which help to ruggedize assembly 10. A battery 36 (FIG. 2) powers LEDs 34 when a switch 38 is activated. Skilled persons will readily recognize, by the mating dovetails on handle 30 and tubes unit 12 and by the presence of removable rear closure 24, which would otherwise not be removable, that tubes unit 12 is removable from handle 30, by sliding the mating dovetails apart.

Figure 3:
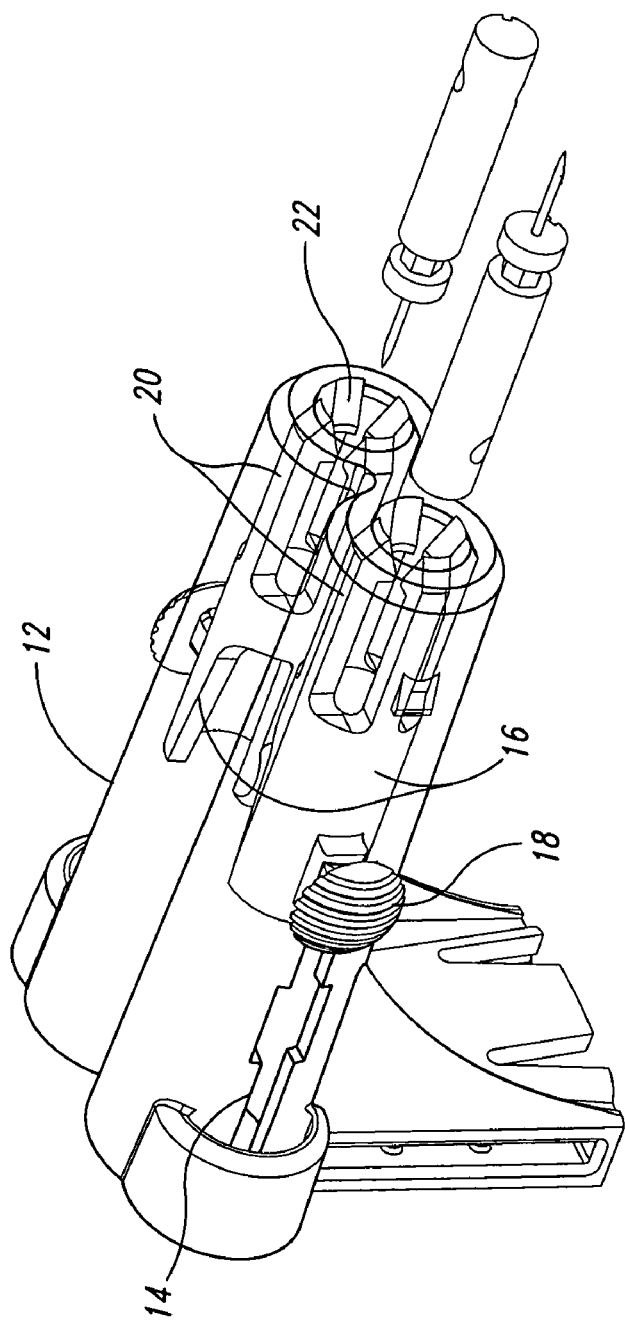
FIG. 3 is a perspective view of a front end of a stun gun dart removing device, shown in proximity to a stun gun dart.

In use, a public safety officer holds assembly 10 by handle 32 and if it is dark, turns on LEDs 34. Referring to FIG. 3, he then places tube 12 about a dart 40 that is to be removed and that has a base 42, having a circumferential groove 44, and a spear 46. The slider arm bumps 22 may fit into the circumferential groove 44 or over then front end of base 42. After this, the officer may pull back on tab 18, thereby pulling slider 16 backwards. This causes arms 16 to be brought slightly inwards, helping to grasp the dart 40. Once dart is locked in place the tool is pulled away from the subject, thereby removing the dart. Once removed from the subject the tab is moved all the way back to the rear of slot 14, to move the dart back, so that it is completely retained within tube 12. Once locked in this retracted position the dart is secured in a safe location. This enables anyone to handle and view the darts without any danger of being stuck and contaminated by the pathogens on the darts.

Viewed more generally, each tube 12 serves as a rigid guide for a slider 16. Moreover, the rigidity of tube 12 permits it to brace against the flesh or clothing of the subject from whom the dart is being removed, steadying the initial effort to lock the arms 20 in place on the dart 40. Once the dart is removed from the subject, the slider permits the dart to be moved back into the tube 12, without the need for touching any part of the dart, so that the dart can be safely locked and housed in the tube 12.

In an alternative preferred embodiment, guides that are not tubes are provided. For example, in a preferred embodiment a dart grasping slider moves along a track, from front to back. A collar supported by the track acts to draw the arms of the slider inwardly, as it is initially retracted backward, so that arms 20 can affirmatively engage the dart 40. Much as the tube does, in the preferred embodiment described above, the track braces against the subject from whom the dart is being removed, to steady the initial contact as the slider is initially moved rearward. In one preferred embodiment the track portion expands laterally at its distal end, to provide a better bracing action. Skilled persons will recognize that differing geometries are possible without diverging from the scope of the invention. For example, the slider could extend through the rear of the tube, rather than the side, or the container could be formed in a shape that would not be circular in cross-section. Tubes that are square or otherwise polygonal in cross-section would not fall outside of the scope of this invention. Moreover, dart capturing mechanisms other than resilient arms 20, are possible. For example a slider could include a resilient or cinching collar that would capture the dart.

The present invention represents a possible great savings for public safety agencies both in man hours and other costs associated with dealing with this new technology. The law enforcement and security officers and all others charged with the use of the device, more safely remove the stun gun darts. Accordingly, jurisdictions may be more willing to permit law enforcement officers to themselves remove the stun gun darts, rather than relying on the very expensive and time consuming alternative of summoning other agencies to do the job.

The preceding description is merely exemplary, rather than limiting. Skilled persons will readily recognize that other embodiments are possible.

The invention claimed is:

1. A stun gun dart removal assembly, comprising:
   (a) a tube, having a front end, and defining an opening at said front end;
   (b) a slider set in said tube and having forward projecting, resilient arms having forward ends and having inwardly facing bumps and said forward ends;
   (c) a slider mover, adapted to permit a user to move said slider forward and backward within said tube;
   (d) an arm closing feature, adapted to move said arms laterally inwardly as said slider is moved from front to back in said tube; and
   (e) whereby said slider can be placed in a position forward in said tube, said assembly can be moved so that said arms laterally surround a portion of a stun gun dart, said slider can be retracted backwardly into said tube causing said arms to close laterally inwardly, capturing said dart with said inwardly facing bumps and moving it backwardly so that it is contained in said tube; and
   (f) wherein said assembly further includes a handle, attached to and supporting said tube and adapted to be grasped by a user and wherein said tube is removable from said handle, so that after said dart is captured said tube, containing said dart, may be removed from said handle and used to store said dart.

2. The assembly of claim 1, wherein said slider mover is a slider tab that protrudes through a slot defined in the side of said tube, thereby permitting a user to move said slider forward and backward by moving said tab forward and backward.

3. The assembly of claim 1, wherein said arm closing feature is a narrowing of said tube from front to back.

4. The assembly of claim 1, wherein at least a portion of said tube is transparent.

5. The assembly of claim 1, further including a front cap to place over said tube, to store said dart safe from human contact.

6. The assembly of claim 1, further wherein the back of said tube is open, and further including a tube back cap, to place over said back opening, to store said dart safe from human contact.

7. A method of removing a stun gun dart from a subject, comprising:
   (a) providing a stun gun dart removal assembly, including:
      (i) a dart container, having an open front end and a back end;
      (ii) a stun gun dart-engaging slider, including forward projecting arms, having forward ends and having inwardly directed bumps on said forward ends and being slidably engaged to and generally within said container, but having a portion outside said container, adapted to be grasped and moved by a human hand; and
      (iii) a handle, adapted to be grasped by a human hand, to which said dart container is removably engaged and by which said dart container is supported;
   (b) placing said slider in a position forward relative to said container;
   (c) placing said assembly so that said slider engages said stun gun dart;
   (d) removing said dart by moving said assembly away from said subject; and
   (e) retracting said slider backward into said container, thereby moving said dart into said container, where it can be safely stored; and
   (f) removing said dart container from said handle and using said dart container to store said dart.

8. The method of claim 7, wherein said container is in the form of a tube.

9. The method of claim 7, wherein said container defines a slot through which a portion of said slider extends, and wherein said steps (b) and (e) are performed by grasping said portion of said slider, to move said slider forward and backward, respectively.

10. The method of claim 7, wherein said container is supported by a handle.

11. The method of claim 7, wherein said assembly further includes a slider engager that causes said slider to more tightly engage said stun gun dart as said slider is initially moved backwardly along said guide.

12. The method of claim 11 wherein said guide is a tube and wherein said slider includes forwardly projecting arms and wherein said slider engager is a narrowing of said tube, which causes said forwardly projecting arms to be brought in laterally as said slider is moved from front to back.

13. The method of claim 12 wherein said forwardly projecting arms each include an inwardly directed bump near the forward end, and wherein said narrowing of said tube brings said bumps inwardly laterally to engage a feature of said stun gun dart.

14. The method of claim 7, wherein at least a portion of said container is transparent, thereby permitting observation of a retained dart.

15. The method of claim 7, further including providing a front cap and placing it on said container.

16. The method of claim 7, further comprising placing a rear cap on said container.

17. The method of claim 7, further comprising placing both a front and a rear cap on said container, thereby sealing said dart in a storage container.

* * * * *